United States Patent [19]

Patel

[11] Patent Number: 4,781,682

[45] Date of Patent: Nov. 1, 1988

[54] CATHETER HAVING SUPPORT FLAPS AND METHOD OF INSERTING CATHETER

[76] Inventor: Piyush V. Patel, 2103 W. Michigan, Midland, Tex. 79701

[21] Appl. No.: 84,827

[22] Filed: Aug. 13, 1987

[51] Int. Cl.[4] ............................................ A61M 29/00
[52] U.S. Cl. ....................................... 604/96; 604/104; 604/105; 604/280
[58] Field of Search .................... 604/93–106, 604/343, 280, 51, 164–166, 267, 344, 348.1

[56] References Cited

U.S. PATENT DOCUMENTS

| | | | |
|---|---|---|---|
| 648,858 | 5/1900 | Dolge | 604/267 |
| 958,854 | 5/1910 | Bunn | 604/267 |
| 3,108,595 | 10/1963 | Overment | 604/105 |
| 3,241,554 | 3/1966 | Coanda | 604/105 |
| 3,397,699 | 8/1968 | Kohl | 604/105 |
| 3,568,659 | 3/1971 | Karnegis | 604/105 |
| 3,605,750 | 9/1971 | Sheridan et al. | 604/280 |
| 3,645,955 | 2/1972 | Flynn | 604/280 |
| 3,885,561 | 5/1975 | Cami | 604/280 |
| 3,938,530 | 2/1976 | Santomieri | 604/105 |
| 4,043,338 | 8/1977 | Homm et al. | 604/105 |
| 4,154,242 | 5/1979 | Termanini | 604/105 |
| 4,195,637 | 4/1980 | Gruntzig et al. | 128/348.1 |
| 4,299,226 | 11/1981 | Banka | 128/344 |
| 4,608,965 | 9/1986 | Anspach, Jr. et al. | 604/105 |
| 4,627,838 | 12/1986 | Cross et al. | 604/105 |
| 4,699,611 | 10/1987 | Bowden | 604/105 |

Primary Examiner—Stephen C. Pellegrino
Assistant Examiner—Colleen M. Reilly
Attorney, Agent, or Firm—Herbert J. Hammond

[57] ABSTRACT

A catheter assembly having a dilating catheter and a guiding catheter. The guiding catheter has elongated, coaxial inner and outer tubes. The distal ends of the inner and outer tubes are connected together. A plurality of passages allow fluid flow through the connection between the inner and outer tubes. A plurality of support flaps are formed on the outer tube by a plurality of longitudinal slits. As the outer tube is moved longitudinally relative to the inner tube, the support flaps bend and move radially outward from the inner tube. The expanded support flaps, within the aorta, help to hold the end of the guiding catheter within the selected coronary artery. Radiopaque rings, mounted on each end of the support flaps, help to determine the location of the support flaps.

2 Claims, 3 Drawing Sheets

CATHETER HAVING SUPPORT FLAPS AND METHOD OF INSERTING CATHETER

BACKGROUND OF THE INVENTION

1. Field of the Invention

This invention relates in general to medical procedures and equipment. In particular, the invention relates to an improved catheter and a method of inserting a catheter into a selected artery.

2. Description of the Prior Art

Catheters are used in the performance of medical procedures, such as coronary angiography and angioplasty. The purpose of angioplasty is to widen the lumen of a coronary artery which has become partially blocked by a stenotic lesion. A stenotic lesion is an abnormal narrowing of an artery due to injury or disease.

The angioplasty procedure involves the introduction of a catheter system into the aorta, by way of the femoral artery, under local anesthesia. The catheter system includes a guiding catheter and a dilating catheter. The distal end of the guiding catheter is inserted into the opening of a selected coronary artery.

The dilating catheter is then passed through the guiding catheter into the coronary artery. The distal end of the dilating catheter is positioned within the stenotic lesion in the coronary artery. A balloon on the end of the dilating catheter is then inflated with a fluid. The balloon forces the blockage open and enlarges the lumen of the artery.

A problem sometimes develops during the procedure, if the dilating catheter has to pass through a tight stenosis or blockage. The reaction force on the catheter assembly may cause the end of the guiding catheter to slip out of the coronary opening. This results in an unstable condition, in which it is much more difficult to pass the dilating catheter through the stenotic lesion.

One possible solution to this problem is to provide an inflatable balloon near the distal end of the guiding catheter. After the guiding catheter has been inserted into the opening of the coronary artery, the balloon is inflated. The balloon engages the inner surface of the coronary artery, and stablizes the guiding catheter. The dilating catheter can then be passed through the guiding catheter and through the stenotic lesion, without forcing the end of the guiding catheter out of the coronary lumen. A catheter assembly and method of this type is described in a co-owned and co-pending patent application.

SUMMARY OF THE INVENTION

The guiding catheter of the invention has an inner and outer tubes which are coaxial. The distal ends of the tubes are connected together. A plurality of longitudinal slits in the outer tube form a plurality of support flaps between the slits. When the outer tube is moved longitudinally relatively to the inner tube, the support flaps move radially. When extended, the support flaps help to hold the distal end of the guiding catheter in the opening of the coronary artery.

A pair of radiopaque rings are mounted on the outer tube, one ring near each end of the slits. These rings facilitate the use of x-rays to determine the exact location of the catheter.

The guiding catheter is introduced into the femoral artery and inserted until the distal ends of the tubes are located within the aorta. The proximate ends of the tubes are then maneuvered to insert the distal ends of the tubes into the selected artery.

A plastic grip, mounted on the proximate end of the outer tube, is then used to move the outer tube longitudinally relative to the inner tube. As the outer tube is moved, the support flaps bend and move radially outward from the inner tube.

DESCRIPTION OF THE PREFERRED EMBODIMENT

Figure 1:
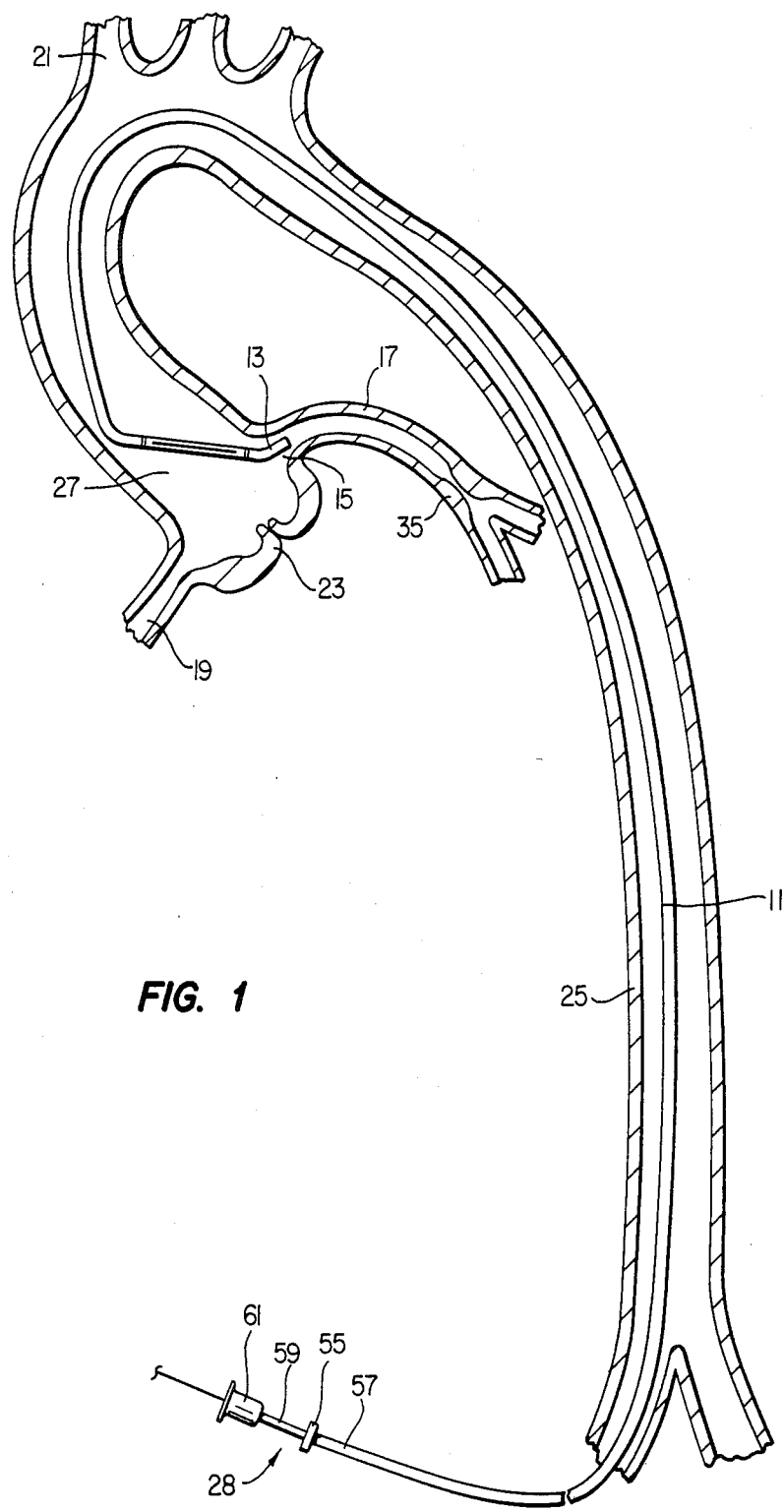
FIG. 1 is a side view of the guiding catheter of the invention, with the distal end of the guiding catheter inserted in the lumen of a coronary artery.
Figure 2:
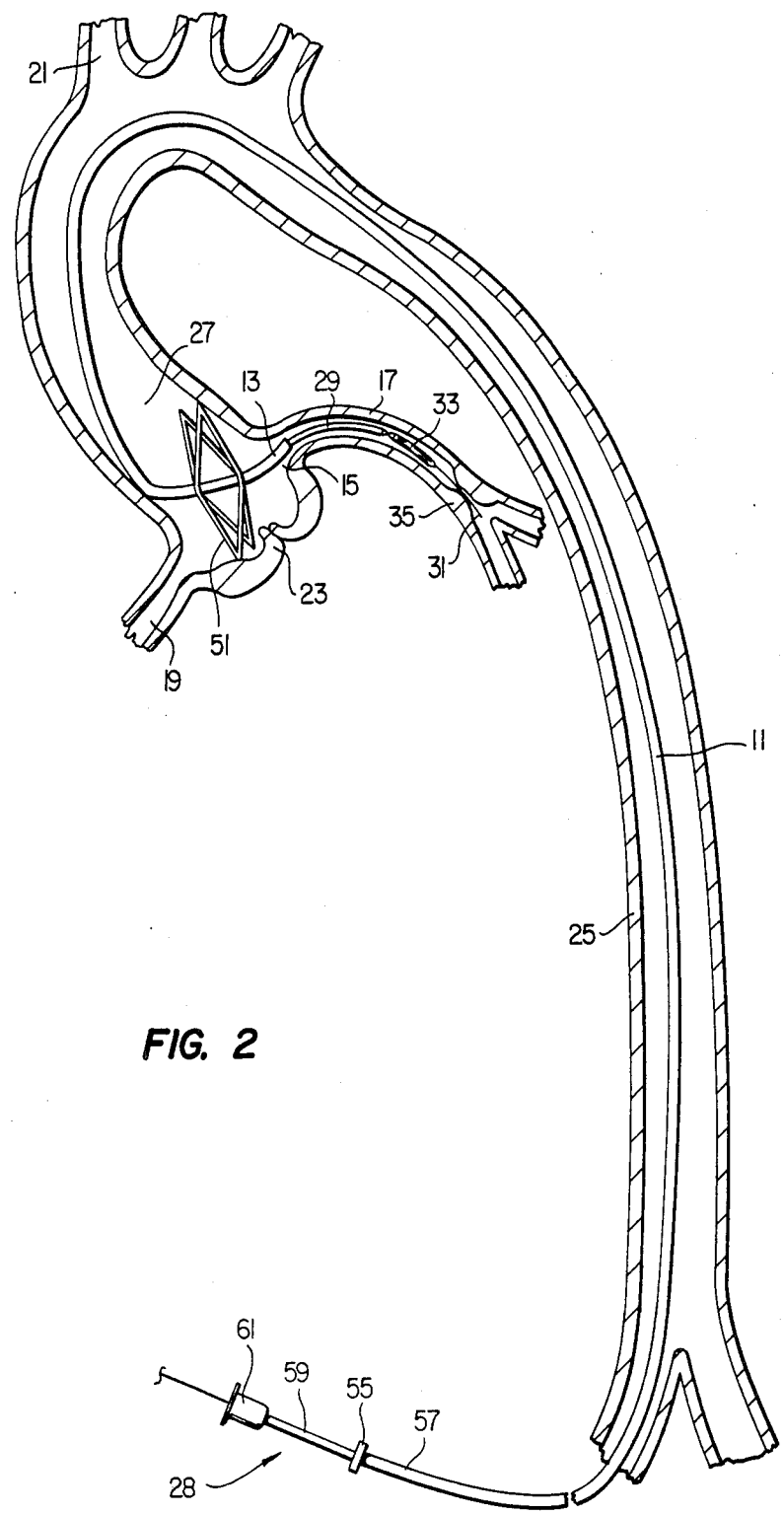
FIG. 2 is a side view of the catheter system of the invention, with the support flaps extended.

FIGS. 1 and 2 show the guiding catheter 11 of the invention, with the distal end 13 of the catheter 11 inserted into the ostium 15 of the left main coronary artery 17. This particular artery 17 has been chosen merely as an example. The catheter 11 of the invention may also be used in the right main coronary artery 19, the bracheocephalic artery 21, or even the aortic valve 23.

The catheter 11 is introduced into the patient's femoral artery 25 and inserted until the distal end 13 is within the patient's aorta 27. The proximate end 28 of the catheter 11 is then maneuvered to insert the distal end 13 into the ostium 15 of the selected artery 17. As shown in FIG. 2, a dilating catheter 29 is then inserted through the guiding catheter 11. The dilating catheter 29 follows a guide wire 31 until a balloon 33 on the dilating catheter 29 is positioned within the stenotic lesion 35. The balloon 33 is then inflated with a fluid to enlarge the lumen of the artery 17.

The guiding catheter 11 of the invention is shown in greater detail in FIGS. 3–6. The guiding catheter 11 has an elongated inner tube 37 and an elongated outer tube 39. The inner and outer tubes 37, 39 are coaxial about a longitudinal axis 40. The distal end 41 of the inner tube 37 is connected to the distal end 43 of the outer tube 39 by a connection 45. The connection 45 has a plurality of passages 47, which allow blood to flow between the tubes 37, 39.

Figure 3:
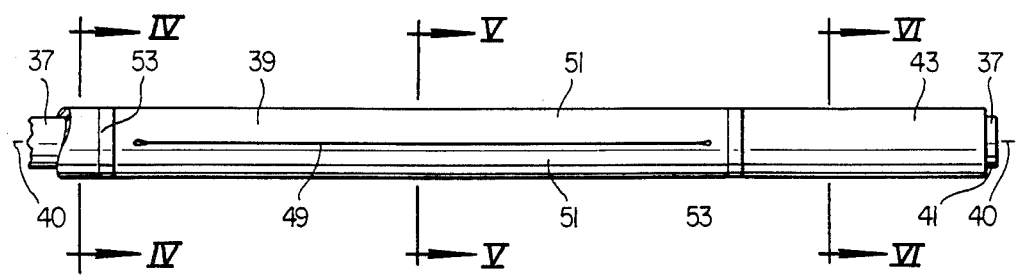
FIG. 3 is a side view of the distal end of the guiding catheter of the invention.
Figure 4:
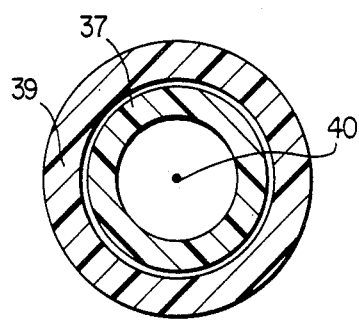
FIG. 4 is a sectional view of the catheter of the invention, as seen along lines IV—IV of FIG. 3.
Figure 5:
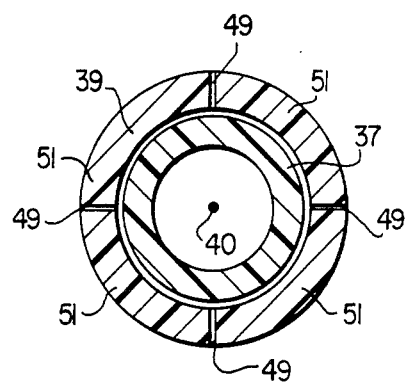
FIG. 5 is a sectional view of the catheter of the invention, as seen along lines V—V in FIG. 3.
Figure 6:
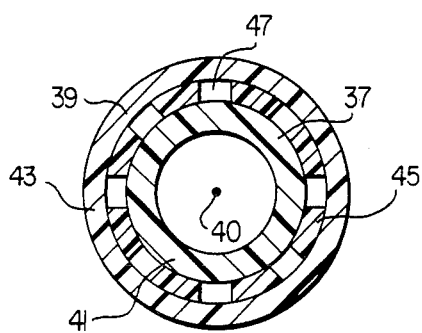
FIG. 6 is a sectional view of the catheter of the invention, as seen along lines VI—VI in FIG. 3.

As shown in FIGS. 3 and 5, the outer tube 39 has four slits 49, which form four support flaps 51 between the slits 49. When the outer tube 39 is moved longitudinally relative to the inner tube 37, the support flaps 51 bend and move radially away from the inner tube 37. In the open position, shown in FIG. 2, the support flaps 51 support the guiding catheter 11 and help to keep the distal end 13 of the guiding catheter 11 from slipping out of the ostium 15 of the coronary artery 17.

Two radiopaque rings 53 are mounted on the outer tube 39. One radiopaque ring 53 is located near each end of the slits 49. These rings 53 facilitate the use of x-rays to determine the location of the catheter 11 in the aorta 27.

As shown in FIG. 2, a plastic grip 55 is located on the proximate end 57 of the outer tube 39. The proximate end 59 of the inner tube 37 may also have a plastic grip 61.

The method of the invention involves first introducing the catheter 11 into the femoral artery 25. The catheter 11 is then inserted through the femoral artery 25 until the distal end 13 of the guiding catheter 11 is located in the aorta 27. The proximate end 28 of the catheter 11 is then maneuvered to insert the distal end 13 of the catheter 11 into the selected coronary artery 17.

Next, the grip 55 on the outer tube 39 is moved longitudinally downward relative to the grip 61 on the inner tube 37. Since the distal ends 41, 43 of the tubes 37, 39 are connected together, the two radiopaque rings 53 are thus moved closer together. The support flaps 51 bend and move radially outward from the inner tube 37. This causes the support flaps 51 to move from the position shown in FIG. 1 to the position shown in FIG. 2.

The dilating catheter 29, including the guide wire 31, is then inserted through the guiding catheter 11 into the coronary artery 17. The dilating catheter 29 can be moved through a tight stenotic lesion 35, and the support flaps 51 will help to keep the end 13 of the guiding catheter 11 from slipping out of the ostium 15 of the artery 17.

The catheter of the invention has several advantages over the prior art. The support flaps 51, in their closed position, can be easily moved through the femoral artery 25. In their opened position, the support flaps 51 support the guiding catheter 11 and help to keep the catheter 11 in the coronary artery 17. The support flaps 51 are easily opened and closed by mechanically manipulating the proximate ends 57, 59 of the tubes 37, 39. The support flaps 51 also help prevent the catheter 11 from sliding too far into the coronary artery 17.

Only the preferred embodiment of the invention has been illustrated. It should be understood that the invention is not limited to the embodiment disclosed, but is capable of numerous rearrangements, modifications, and substitutions of parts and elements, without departing from the scope of the invention.

I claim:

1. A method of inserting a catheter assembly for use in performing coronary angioplasty, wherein the catheter assembly comprises a dilating catheter having a balloon, an elongated inner tube coaxial with the dilating catheter having a proximate end and a distal end, an elongated outer tube coaxial with the inner tube having a proximate end and a distal end, the distal end of the outer tube being connected to the distal end of the inner tube, wherein the connection between the distal end of the inner tube and the distal end of the outer tube has a plurality of passages for blood flow between the inner tube and the outer tube, a plurality of support flaps formed on the outer tube by a plurality of longitudinal slits capable of radial movement when the outer tube is moved longitudinally relatively to the inner tube, the method comprising the steps of:

introducing the catheter assembly into a femoral artery until the distal ends of the inner and outer tubes of the catheter assembly are located within the patient's aorta;

maneuvering the proximate ends of the inner and outer tubes to insert the distal end of the inner and outer tubes into a selected artery;

moving the proximate end of the outer tube longitudinally relative to the inner tube, in order to cause a plurality of support flaps to move radially outward from the inner tube and to support the distal ends of the inner and outer tubes in the selected coronary artery;

inserting a dilating catheter having a balloon into the selected artery; and inflating the balloon with a fluid to enlarge the lumen of the selected artery for allowing the dilating catheter to pass through the selected artery and to perform the necessary angioplasty.

2. A catheter assembly for use in performing coronary angioplasty, comprising:

a dilating catheter;

an elongated inner tube, coaxial with the dilating catheter, having a proximate end and a distal end;

an elongated outer tube, coaxial with the inner tube, having a proximate end and a distal end, the distal end of the outer tube being connected to the distal end of the inner tube, wherein the connection between the distal end of the inner tube and the distal end of the outer tube has a plurality of passages for blood flow between the inner tube and the outer tube;

a plurality of support flaps, formed on the outer tube by a plurality of longitudinal slits, wherein the support flaps move radially when the outer tube is moved longitudinally relative to the inner tube;

a pair of radiopaque rings, mounted on the outer tube, one ring near each end of the slits; and a plastic grip, mounted on the proximate end of the outer tube.

* * * * *